United States Patent
Dougherty-Shah

(10) Patent No.: US 7,470,273 B2
(45) Date of Patent: Dec. 30, 2008

(54) TOOL FOR INTERVERTEBRAL IMPLANT MANIPULATION

(75) Inventor: Gretchen Dougherty-Shah, Wayne, NJ (US)

(73) Assignee: EBI, LLC, Parsippany, NJ (US)

(*) Notice: Subject to any disclaimer, the term of this patent is extended or adjusted under 35 U.S.C. 154(b) by 825 days.

(21) Appl. No.: 10/877,100

(22) Filed: Jun. 25, 2004

(65) Prior Publication Data

US 2005/0288788 A1    Dec. 29, 2005

(51) Int. Cl.
*A61B 17/58* (2006.01)
*A61F 2/44* (2006.01)

(52) U.S. Cl. .................. 606/86 A; 623/17.16

(58) Field of Classification Search .............. 606/53, 606/86, 99, 86 R, 86 A; 623/17.11–17.16
See application file for complete search history.

(56) References Cited

U.S. PATENT DOCUMENTS

| | | | |
|---|---|---|---|
| 5,766,252 A | 6/1998 | Henry et al. | |
| 5,865,845 A | 2/1999 | Thalgott | |
| 5,888,227 A | 3/1999 | Cottle et al. | |
| 5,897,556 A | 4/1999 | Drewry et al. | |
| 5,951,564 A * | 9/1999 | Schroder et al. | 606/100 |
| 6,039,762 A | 3/2000 | McKay | |
| 6,143,032 A | 11/2000 | Schafer et al. | |
| 6,245,108 B1 | 6/2001 | Biscup | |
| 6,432,106 B1 | 8/2002 | Fraser | |
| 6,458,159 B1 | 10/2002 | Thalgott | |
| 6,562,072 B1 | 5/2003 | Fuss et al. | |
| 6,579,318 B2 | 6/2003 | Varga et al. | |
| 6,676,703 B2 | 1/2004 | Biscup | |
| 6,699,288 B2 | 3/2004 | Moret | |
| 6,716,245 B2 | 4/2004 | Pasquet et al. | |
| 6,719,794 B2 * | 4/2004 | Gerber et al. | 623/17.11 |
| 6,974,480 B2 * | 12/2005 | Messerli et al. | 623/17.16 |
| 7,060,073 B2 * | 6/2006 | Frey et al. | 606/85 |
| 2002/0143400 A1 | 10/2002 | Biscup | |
| 2002/0193880 A1 | 12/2002 | Fraser | |
| 2003/0023312 A1 | 1/2003 | Thalgott | |
| 2003/0153975 A1 | 8/2003 | Byrd, III et al. | |

* cited by examiner

*Primary Examiner*—Eduardo C Robert
*Assistant Examiner*—Ellen Rust
(74) *Attorney, Agent, or Firm*—Harness, Dickey, & Pierce, P.L.C.

(57) ABSTRACT

A tool for inserting or removing an intervertebral implant. The tool includes a first arm having a curved tip adapted for engaging a side wall groove of the intervertebral implant and a second arm pivotably coupled to the first arm. The first arm defines a first concave distal surface extending continuously from the curved tip and the second arm defines a second concave distal surface. The first and second concave distal surfaces define an engagement surface engageable to a substantially complementary convex end wall of the intervertebral implant.

4 Claims, 6 Drawing Sheets

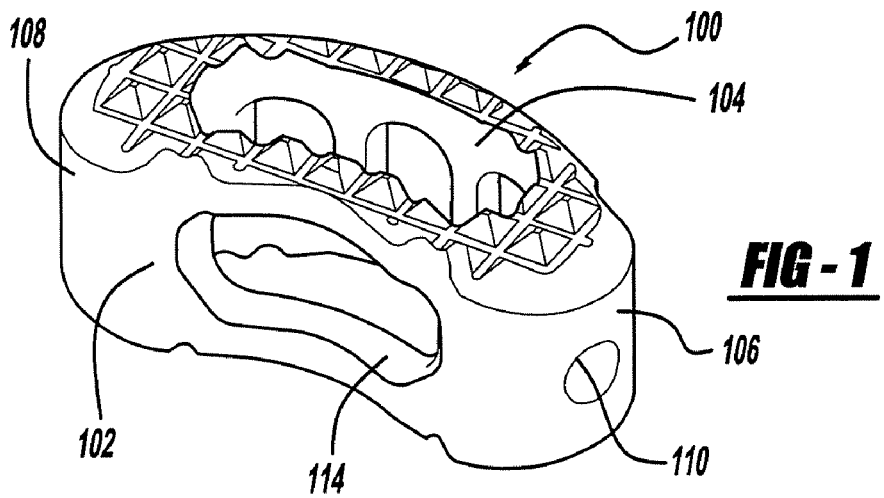
*FIG - 1*
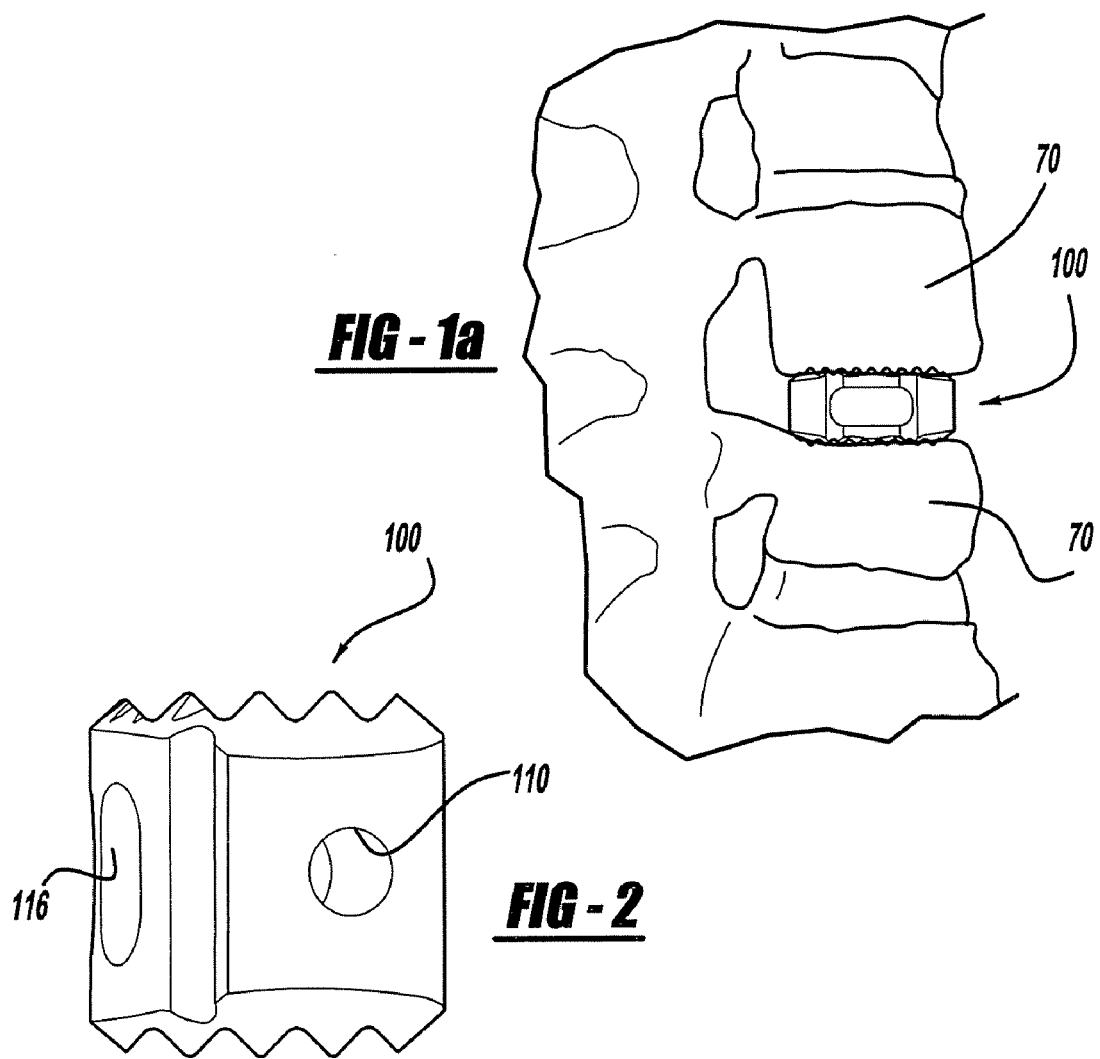
*FIG - 1a*
*FIG - 2*

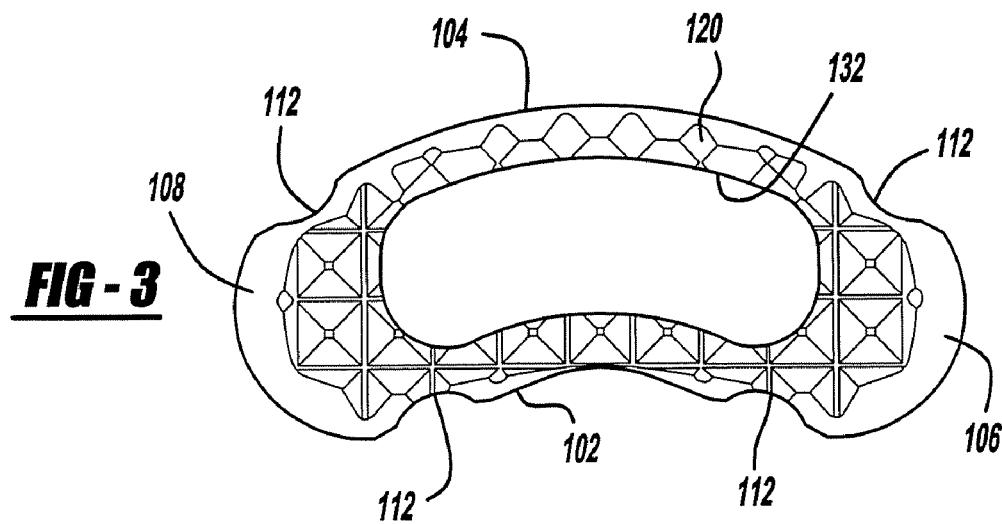
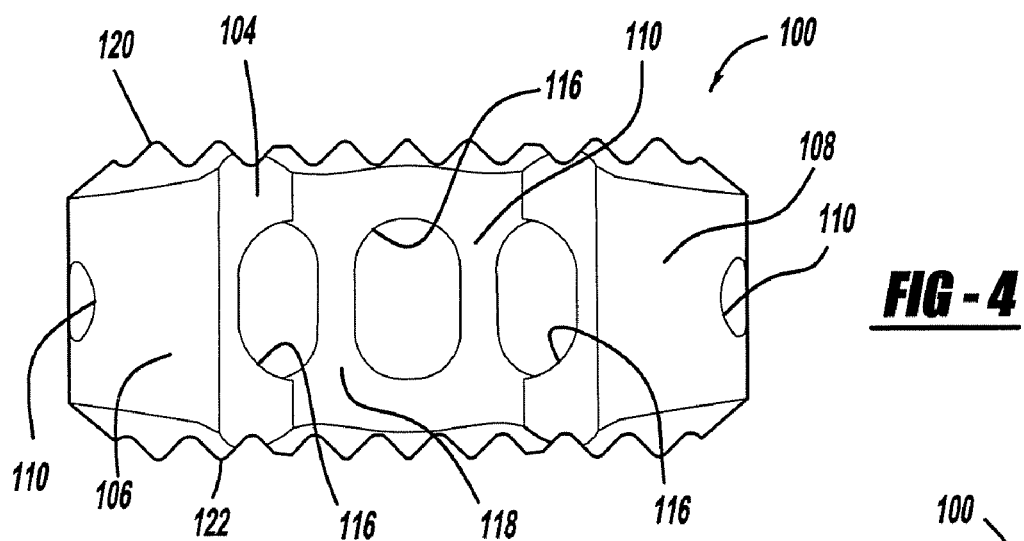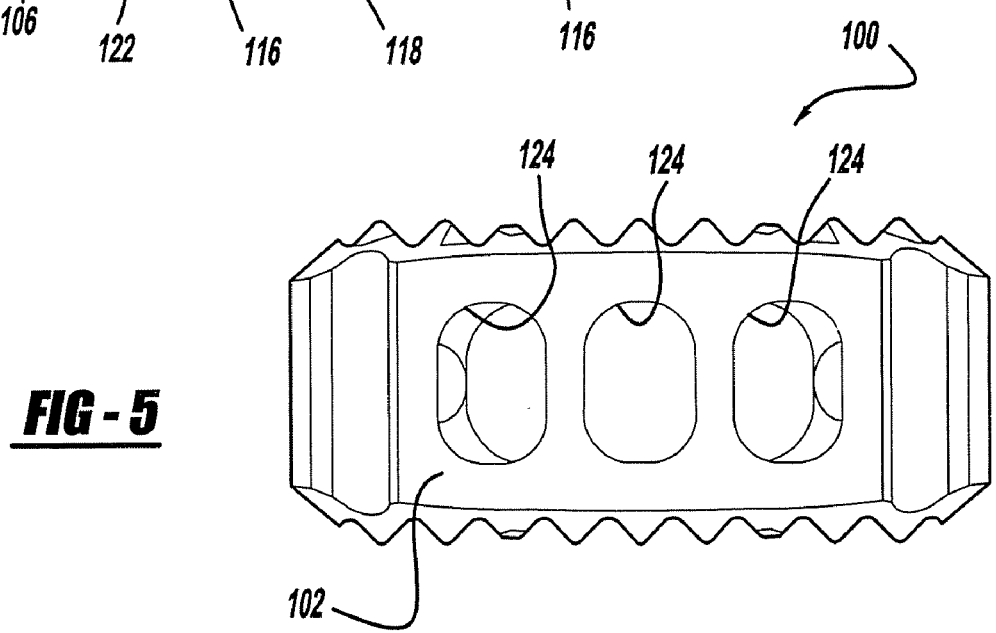

TOOL FOR INTERVERTEBRAL IMPLANT MANIPULATION

Spinal fusion can be used to treat degenerative disc disease, spondylolisthesis, nerve compression associated with lower back pain and other pathologies of the spine. During spinal fusion surgery, a prosthetic implant is inserted between two vertebrae. Although various spinal implants have been developed, there is still a need for easily implantable and accessible prosthetic devices that promote tissue growth.

SUMMARY

The present teachings provide an intervertebral implant. The intervertebral implant includes a hollow body formed by first and second side walls and first and second end walls. The first side wall defines an engagement groove adjacent the first end wall for engaging an arm of an implant tool.

The present teachings also provide a tool for inserting or removing an intervertebral implant. The tool includes a moveable arm having a curved tip adapted for engaging a side wall groove of the intervertebral implant.

The present teachings also provide a method for packing a hollow intervertebral implant. The method includes implanting the intervertebral implant between two vertebrae such that an elongated opening of a side wall of the implant is accessible during surgery, and introducing biological materials through the elongated opening into the implant after implantation.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an intervertebral implant according to the present teachings;

FIG. 1A is an environmental view of an intervertebral implant according to the present teachings;

FIG. 2 is an end view of an intervertebral implant according to the present teachings;

FIG. 3 is a top view of an intervertebral implant according to the present teachings;

FIG. 4 a posterior side view of an intervertebral implant according to the present teachings;

FIG. 5 an anterior view of an intervertebral implant according to the present teachings;

DETAILED DESCRIPTION

Figure 6:
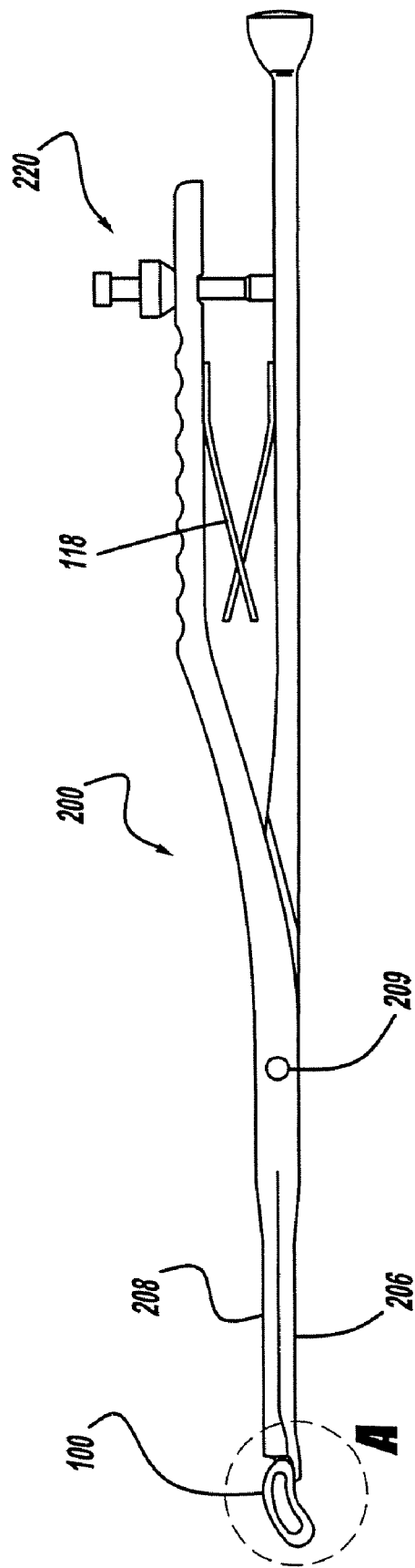
FIG. 6 is a top view of an intervertebral implant and an implant tool according to the present teachings.

The following description is merely exemplary in nature and is in no way intended to limit the invention, its application, or uses.

Referring to FIG. 1, an exemplary intervertebral implant 100 according to the present teachings includes a hollow body with a central opening 132 defined by first and second side walls 102, 104 joined by first and second end walls 106, 108. The intervertebral implant 100 can be anatomically contoured, with the first side wall 102 being a posterior concave wall and the second side wall 104 being an anterior convex wall. Referring to FIG. 1A, the intervertebral implant 100 can be inserted between two vertebrae 70 during a spinal fusion procedure using, for example, a transforaminal posterior approach.

Referring to FIGS. 1-5, the first wall 102 can include one large elongated opening 114, as illustrated in FIG. 1, or several smaller openings 124, as illustrated in FIG. 5. The second side wall 104 can also include several openings 116 separated by posts 118 that provide structural rigidity. The central opening 32 and the side wall openings 114, 116 provide an open cage shape for the intervertebral implant 100, thereby promoting bone in-growth and allowing post-implantation visualization of the fusion mass on an anterior-posterior radiograph. Additionally, the open cage structure together with the elongated opening 114 facilitates packing the intervertebral implant 100 with bone graft and other growth promoting materials before or after implantation, at the discretion of the surgeon.

The intervertebral implant 100 can include superior and inferior engagement formations 120, 122 for engaging the vertebrae. The engagement formations 120, 122 can be pyramidal or otherwise shaped teeth, serrations, undulations, ridges, and the like. The end walls 106, 108 can be curved or chamfered or include curved and chamfered portions for ease of insertion. The openings 116, 124 and 116 can also have various shapes and sizes for improving visualization, maintaining structural stability, promoting ingrowth, and facilitating graft packing pre- and post-implantation.

Figure 7:
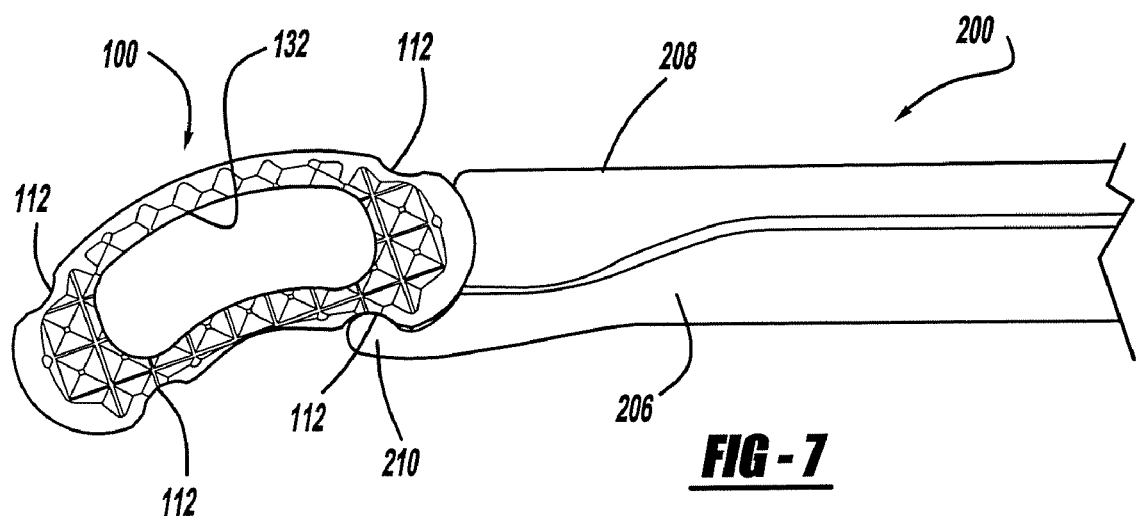
FIG. 7 is an enlarged view of detail A of FIG. 7.
Figure 8:
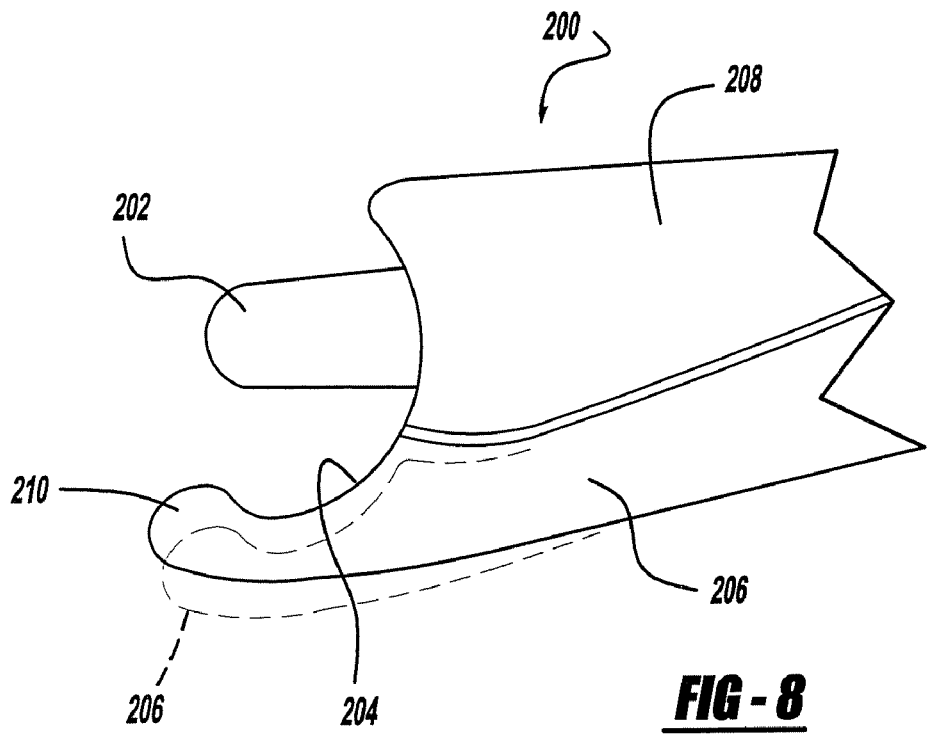
FIG. 8 is an enlarged view of the implant tool of FIG. 7.
Figure 9:
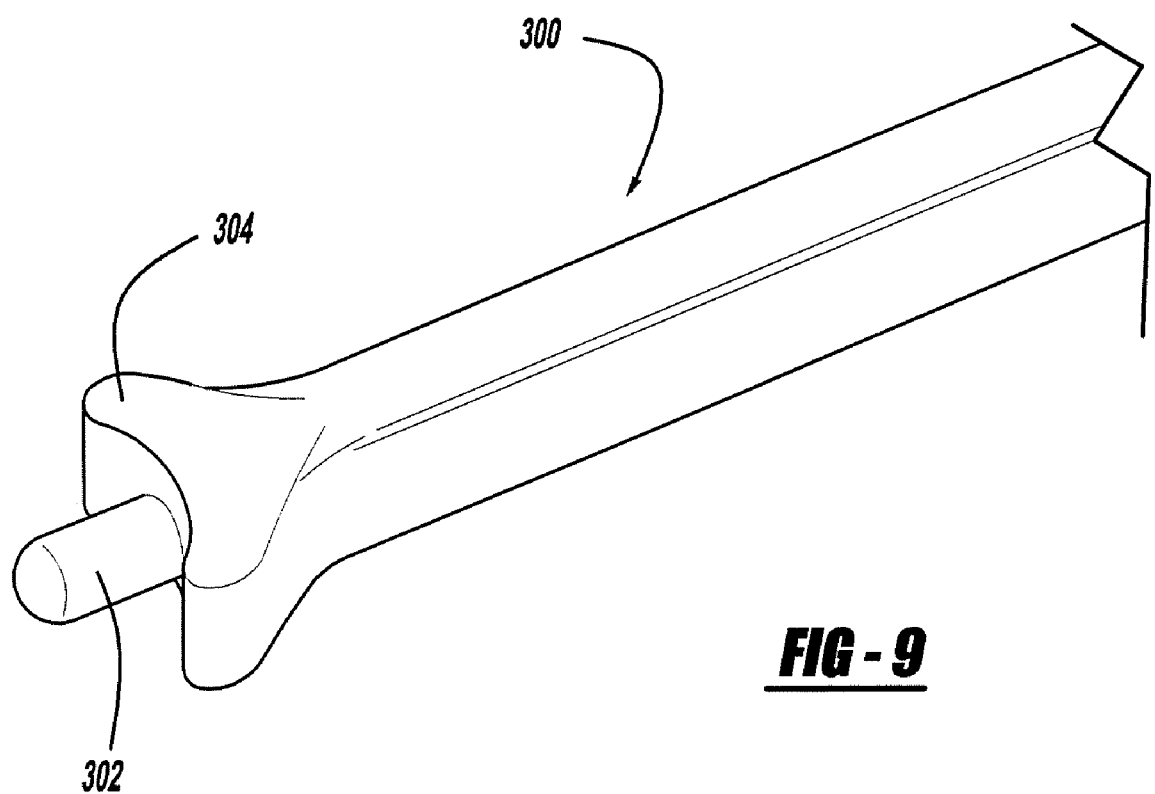
FIG. 9 is a perspective view of an implant tool for an intervertebral implant according to the present teachings.

At least one of the end walls 106, 108 can include an end opening 110 for receiving a peg 202, 302 of an implant tool, such as, an inserter 200, illustrated in FIGS. 6-8, or an impactor 300, illustrated in FIG. 9. The inserter 200 can have a curved engagement surface 204 substantially complementary to the profile of the end walls 106, 108. The inserter 200 can include first and second arms 206, 208 that are pivotably coupled for scissor-like relative movement about a pivot axis 209.

The first arm 206 is movable relative to the second arm 208 between a first position and a second position. The first position is generally shown throughout the drawings in solid lines. The second position is shown in FIG. 8 in phantom lines. In the first position, the first arm 206 cooperates with the peg 202 to engage and non-rotatably clamp the implant 100. In the second position, the implant may be released from the inserter 200.

The end surfaces of the arms 206, 208 define the curved engagement surface 204, which can be asymmetric, as illustrated in FIG. 7, although an inserter with a symmetric engagement surface can also be used. The peg 202 can extend from the end surface of the second arm 208. The first arm 206 can terminate at a rounded tip 210 that is shaped to engage a similarly shaped groove or recess 112 which is formed on the first sidewall 102 adjacent to the first end wall 110, as shown in FIG. 3.

Figure 10:
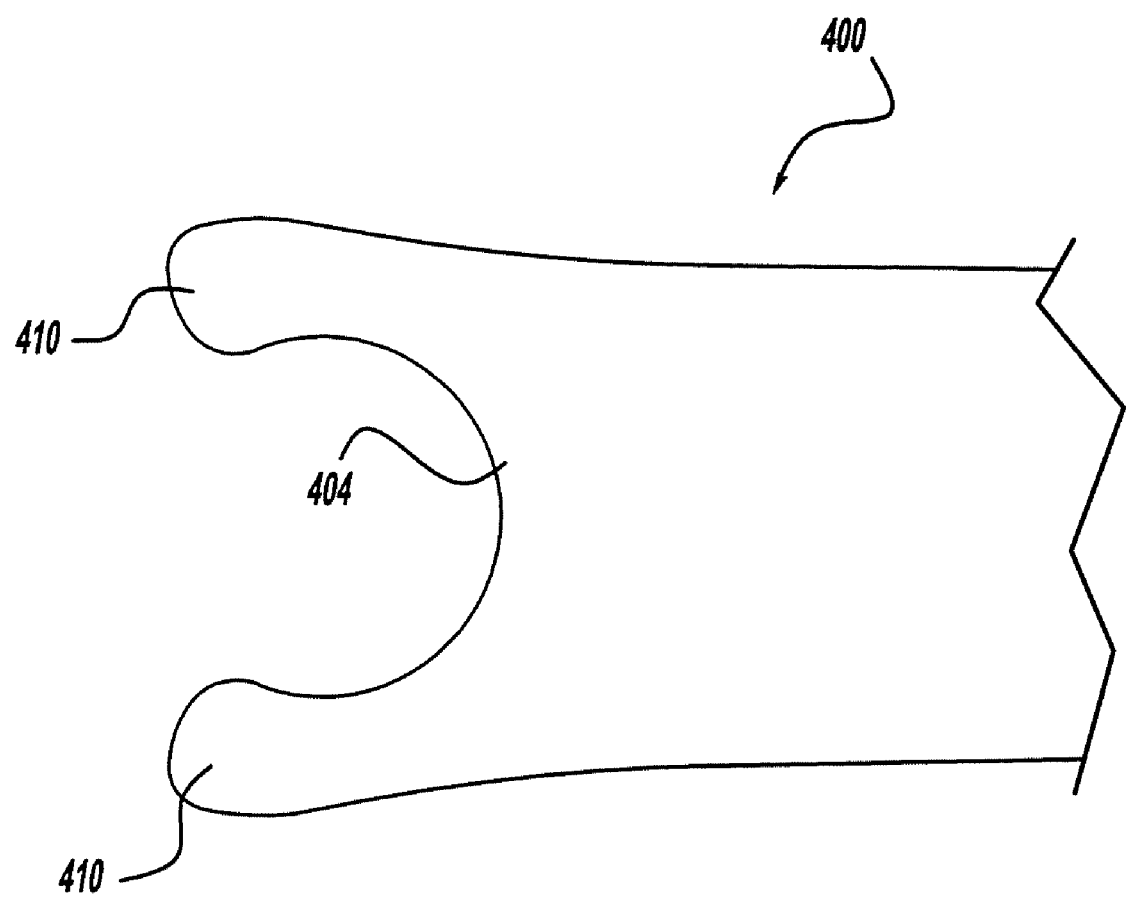
FIG. 10 is a top view of an implant tool according to the present teachings.

The combination of peg 202 and arm tip 210 allow the intervertebral implant 100 to be grasped securely by the inserter 200 while keeping the width of the inserter to a narrow dimension. A similar groove 112 can be formed at a corresponding location at the other end of the first wall 102, and another pair of grooves 112 can be formed on the second wall 104. Referring to FIG. 10, another implant tool, such as an inserter or remover 400 lacking a peg and having a symmetric engagement surface 404 with two arm tips 410 that can be received in corresponding grooves 112 can be used for inserting and or removing the intervertebral implant 100.

The inserter 200 can be used to hold the intervertebral implant 100 for insertion in an intervertebral space as follows. The arms 206, 208 of the inserter 200 are opened, and the peg 202 of the second arm 208 is inserted through the end opening 110. The arms 206, 208 are then closed, such that the tip 210 of the first arm 206 is received in the groove 112 to hold and stabilize the intervertebral implant 100. The arms 206, 208 can be secured in the closed position against the opening action of springs 118 by a lock 220, such as, for example, a bolt and nut.

After the intervertebral implant 100 is inserted in the intervertebral space, the impactor 300 can be used to more precisely position the intervertebral implant 100. The impactor 300 can have an end surface 304 from which the peg 302 extends. The end surface 304 can be straight, or curved and symmetric, or curved and asymmetric. The peg 302 is inserted into the end opening 110 of the intervertebral implant 100, which is then pushed into location by the end surface 304.

According to a method of the present teachings, the intervertebral implant 100 can be selectively packed with bone graft and other biologic materials either before or after implantation in situ. For example, prior to implantation, bone graft or other biological materials can be principally introduced through the open upper and lower ends of the opening 32. As the intervertebral implant 100 is in situ during surgery, the bone graft and other biological materials can be introduced through the elongated opening 104. In this regard, the elongated opening 104 is oriented to face posteriorly and therefore readily accessible for packing.

The intervertebral implant 100 can be made of biocompatible materials, including metals and metal alloys such as titanium alloys, ceramics, resorbable and non-resorbable polymers, and combinations thereof. The inserter 200, the impactor 200 and the inserter/remover 400 can be made of metals or metal alloys, such as stainless steel, titanium alloys, etc.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A tool for inserting or removing an intervertebral implant, the tool comprising:
   a first arm having a proximal end and a distal end, the distal end of the first arm defining a substantially concavely curved first arm surface;
   a second arm having a proximal end and a distal end, the second arm pivotably connected to the first arm for movement between a first position for engaging an intervertebral implant and a second position for releasing the intervertebral implant, the distal end of the second arm extending beyond the distal end of the first arm, the distal end of the second arm defining a substantially concave second arm surface and a substantially convexly rounded tip directly adjacent the second arm surface, the first and second arm surfaces defining a concavely curved engagement surface substantially complementary to a convex profile of an end wall of an intervertebral implant; and
   a peg extending outwardly from a central portion of the first arm surface of the distal end of the first arm, the peg substantially coaxial to the first arm, the peg receivable in an opening of the end wall of the intervertebral implant; and
   wherein the rounded tip is receivable in a recess of a sidewall of the implant, the rounded tip facing the peg, such that the implant can be non-rotatably clamped between the peg and the rounded tip.

2. The tool of claim 1, wherein the curved engagement surface is non symmetric.

3. The tool of claim 1, wherein the first and second arms are biased in the second position.

4. The tool of claim 3, further comprising a lock to secure the arms in the first position.

* * * * *